United States Patent [19]

Wissler et al.

[11] Patent Number: 4,465,669

[45] Date of Patent: Aug. 14, 1984

[54] ANGIOTROPINS OF LEUKOCYTES AND INFLAMED TISSUE, PROCESS FOR THEIR BIOTECHNICAL PREPARATION, AND PHARMACEUTICAL COMPOSITIONS THEREOF

[75] Inventors: Josef H. Wissler; Wolfgang Schaper, both of Bad Nauheim, Fed. Rep. of Germany

[73] Assignee: Max-Planck Gesellschaft zur Forderung der Wissenschaften e.V., Göttingen, Fed. Rep. of Germany

[21] Appl. No.: 357,814

[22] Filed: Mar. 15, 1982

[30] Foreign Application Priority Data

Mar. 18, 1981 [DE] Fed. Rep. of Germany ....... 3110560

[51] Int. Cl.³ .......................... A61K 37/00; C12N 5/02
[52] U.S. Cl. ..................................... 424/177; 424/85; 435/68; 435/241
[58] Field of Search ..................... 435/68; 424/177, 85, 424/101; 435/241

[56] References Cited

U.S. PATENT DOCUMENTS 4,229,531  10/1980  Tolbert ................................ 435/68

OTHER PUBLICATIONS

Bluethmann—Chem. Abst., vol. 91 (1979), p. 71125j.
Kumamoto et al.—Chem. Abst., vol. 94, (1981), p. 62,442v.

Primary Examiner—Sam Rosen
Attorney, Agent, or Firm—Cooper, Dunham, Clark, Griffin & Moran

[57] ABSTRACT

The invention relates to new angiotropins of leukocytes and inflamed tissue which have the biological and physicochemical properties stated in the patent claims. The compounds selectively stimulate the directional growth of blood vessels and lead to a neovascularization of tissue. The invention also relates to a biotechnical process for preparing and isolating the angiotropins and to pharmaceutical compositions containing them.

36 Claims, 8 Drawing Figures

CHEMOTROPISM (DIRECTIONAL GROWTH) OF SCLERO-LIMBAL BLOOD VESSELS AND NEOVASCULARIZATION OF THE CORNEA OF THE RABBIT EYE BY 10 fmol OF HIGHLY PURIFIED, MORE THAN 100,000 TIMES ENRICHED MONOCYTO-ANGIO-TROPIN (MAT) FROM MITOGEN-STIMULATED MONOCYTES OF PORCINE BLOOD. THE BLUE SPOT (EXTRAVASAL EVAN'S BLUE) SHOWS THE INCREASED PERMEABILITY OF THE SPROUTING VESSEL TIPS.

CHEMOTROPISM (DIRECTIONAL GROWTH) OF SCLERO-LIMBAL BLOOD VESSELS AND NEOVASCULARIZATION OF THE CORNEA OF THE RABBIT EYE BY 100 fmol OF HIGHLY PURIFIED, MORE THAN 100,000 TIMES ENRICHED GRANULOCYTO-ANGIO-TROPIN (GAT) FROM GRANULOCYTIC LEUKOCYSTES OF PORCINE BLOOD.

FIG. 3 ABSORPTUON SPECTRUM OF MONOCYTO-ANGIOTROPIN IN WATER AT 20°C. EXTINCTION SCALE (0-100) E = 0-2, AT A LIGHT PATH d = 1 cm.

ABSORPTION SPECTRUM OF GRANULOCYTO-ANGIOTROPIN IN WATER AT 20 C. EXTINTION SCALE (0-100) E = 0-2 AT A LIGHT PATH d = 1 cm.

STANDARD-PYROGEN ASSAY ACCORDING TO EUR. PHARMACO-
POEIA 1975, VOL. II: RECTAL TEMPERATURE OF A RABBIT
PRIOR TO (V, A), DURING (*) AND AFTER (P) INTRAVENOUS
APPLICATION OF 5 μg MONOCYTO-ANGIOTROPIN (MAT),
CORRESPONDING TO ABOUT 0.3 nmol MAT/kg ANIMAL.

STANDARD-PYROGEN ASSAY ACCORDING TO EUR. PHARMACOPOEIA 1975, VOL. II: RECTAL TEMPERATURE OF A RABBIT PRIOR TO (V, A), DURING (*) AND AFTER (P) INTRAVENOUS APPLICATION OF 5 μg MONOCYTO-ANGIOTROPIN (MAT), CORRESPONDING TO ABOUT 0.3 nmol MAT/kg ANIMAL.

STANDARD-PYROGEN ASSAY ACCORDING TO EUR. PHARMACO-POEIA 1975, VOL. II: RECTAL TEMPERATURE OF A RABBIT PRIOR TO (V, A), DURING (*) AND AFTER (P) INTRAVENOUS APPLICATION OF 5 µg MONOCYTO-ANGIOTROPIN (MAT), CORRESPONDING TO ABOUT 0.3 nmol MAT/kg ANIMAL.

CHEMOTROPISM (DIRECTIONAL GROWTH) OF SCLERO-LIMBAL BLOOD VESSELS AND NEOVASCULARIZATION OF THE CORNEA OF THE RABBIT EYE BY 30 fmol OF MONOCYTO-ANGIOTROPIN (MAT) ISOLATED IN HIGH PURITY FROM INFLAMED TISSUE (INFARCTED CANINE HEART MUSCLE TISSUE). THE REACTION IS FIRST-TIME PROOF OF FORMATION AND PRESENCE OF CHEMOTROPIC PROTEIN MITOGENS FOR DIRECTIONAL SPROUTING OF BLOOD VESSELS IN INFLAMED TISSUE SITES, ESPECIALLY IN THE INFARCTED HEART MUSCLE.

FIG. 6

ANGIOTROPINS OF LEUKOCYTES AND INFLAMED TISSUE, PROCESS FOR THEIR BIOTECHNICAL PREPARATION, AND PHARMACEUTICAL COMPOSITIONS THEREOF

BACKGROUND OF THE INVENTION

"Blood vessels go where they are needed", see A. A. Liebow in Handbook of Physiology, Section 2: Circuation, vol. 2, p. 1251–1276, Amer. Physiol. Soc. Washington, 1965. The homeostasis of the body and its organs and tissues depends on regulatory mechanisms of angiogenesis (lateral and directional growth of blood vessel capillaries). This homestasis of blood vessel patterns influences tissue repair and wound healing, tissue neoformation in embryonogenesis and in reproductive cycles as well as survival, out-growth, regression and destruction of tumors, grafts and non-vascularized tissues. All these are examples of tissue regeneration processes.

It has been assumed that, as morphogens, soluble mediators may induce and regulate neoformation of blood vessels upon accumulation of leukocytes in the course of inflammatory processes; see A. A. Leibow, loc. cit.; W. Schaper (ed.), Pathophysiology of Myocardial Perfusion, Elsevier-North Holland, Amsterdam 1979; H. I. Peterson, (ed.) "Tumor Blood Circulation" CRC Press, Boca Raton 1979, with further references.

The destruction of tissue in inflammations caused by non-immunological and immunological processes induces the formation of different endogenous substances (mediators and hormones). They regulate the complex steps of activation of the inflammation and tissue regeneration processes. The mediators are formed either by limited and regulated proteolysis of plasma and serum protein factors as humoral mediators; or they are liberated by active secretion and/or cell lysis from cells and tissues as cellular mediators. Especially the mediators and hormones are important as specific carriers of chemical information which are formed and secreted by leukocytes in the course of cell proliferation processes (mitosis processes). They are components of the body's defence system whose systemic and local activation they regulate. The mediators contribute to the removal and detoxification of destroyed body's own components and/or intruded foreign components. In addition, by regulation of cell proliferation and tissue growth processes in wound-healing, they contribute to the restoration of physiological functions of the organism. As the classical hormones of endocrine glands, inflammatory mediators are trace components of tissues or blood and are present in very minute concentrations only. Experimental evidence shows that only up to 5,000 of such mediator protein molecules can be maintained in a steady state equilibrium by a cell in the mitotic cycle in its surrounding medium.

The sprouting of blood vessels occurs by chemotropism. Chemotropism is a reaction by which the direction of hyperplastic or hypertropic growth of tissues or organisms is determined by chemical substances in the cellular environment. The growth can occur in direction to the substance along its increasing concentration gradient; or it can occur away from the substance along its decreasing concentration gradient. Accordingly, directional growth is called positive and negative chemotropism, respectively; see W. G. Rosen, Quart. Rev., Biol., vol. 37 (1962) p. 242 to 259 with further references.

Specifically acting, endogenous chemical self-components with mitogen activity (chemotropic mitogens) which cause chemotropism in blood vessels along their increasing concentration gradient, are called by definition "angiotropins". Angiogenesis is a common characterstic of most inflammation, tissue regeneration and tissue growth processes, such as those caused by bacterial infections, in tumors and heart muscle infarction. The first inducing steps are endogenous or exogenous tissue injury processes, such as ischemic and immunological tissue injury processes, respectively.

Numerous factors which themselves are not chemotropically active, may indirectly induce directional growth of blood vessels. They are called angiotropinogens. These factors include known tissue damaging substances, such as silver nitrate, sodium hydroxide and endotoxins; see C. H. Fromer et al., Amer. J. Pathol.. vol. 82, (1976), p. 157 to 170.

Such exogenous foreign substances as endotoxins have a strong indirect biological action on tissue systems; see O. Lüderitz, Angew. Chemie 82 (1970), p. 708 to 722. It is known that, on the one hand, toxins activate blood plasma protein systems, such as the kinine and the complement protein systems. On the other hand, they display mitogenic activity on mononuclear leukocytes (B-cell-mitogen); see J. Andersson et al. J. Exp. Med. 137 (1973), p. 943 to 953.

The participation of soluble tissue and cell extracts in mechanisms leading to blood vessel growth has already been postulated; see Liebow, loc. cit. M. Klagsbrun et al., Cancer Res., vol. 136 (1976), p. 110 to 114, D. Tuan et al., Biochemistry, vol. 12 (1973), p. 3159 to 3165 and J. Folkman et al., J. Exp. Med. vol. 133 (1971), p. 975 to 988 have been able to prepare crude extracts from tumors. The composition of such complex mixtures of substances which are represented by crude extracts of tumor tissues has not been further characterized biologically or chemically. However, these authors have been able to show that such extracts can stimulate blood vessel growth. A molecular estimation of activity distributions of such complex mixtures of crude extracts of tissues suggested that the blood vessel growth stimulating activity may be associated with molecular weight distributions larger than 100,000 dalton. L. U. Mostafa et al., J. Path. vol. 132 (1980), p. 191 to 215 have shown that such crude tumor extracts are also chemotactically active for leukocytes. Thus, such extracts may also cause a leukocyte accumulation. This shows that the apparent effects induced by these crude tissue extracts are supposedly based on indirect mitogen action, namely by means of the accumulation of leukocytes. More recently, blood vessel growth-stimulating activity has been associated with low molecular weight products such as prostaglandins; see R. Baserga (ed.): Tissue Growth factors. Handbook of Experimental Pharmacology, Springer Verlag, Berlin 1981, with further references.

However, prostaglanidins form a class of complex unsaturated fatty acid derivatives which are known to cause non-specific inflammatory processes, and thus possibly indirectly angiogenesis; see G. Weissman, B. Samuelsson and R. Paoletti (eds.): Adv. Inflammation Res., Raven Press, New York 1980.

Accordingly, Polverini et al., Nature, vol. 269 (1977) p. 804 to 806 have shown that phagocytizing macrophages can produce blood vessel growth-stimulating activities of unknown nature. In addition, it has been found that granulocytes and lymphocytes may be also a source of such blood vessel growth-stimulating activities; see C. H. Fromer et al., loc. cit.; Peterson et al. loc. cit.

The possibility that blood vessel growth-stimulating activities stem from leukocytes accumulated at reaction sites of inflammation has also been suggested by several facts. Thus, for preparation of such crude soluble blood vessel growth-stimulating activities from tissues, various non-physiological conditions have been used. They include the extraction of tissues by organic solvents, the degradation of tissues by tryosin and exposure of tissue extracts to hydrochloric acid. It is known that such extreme conditions may cause non-physiological changes in the structure and activity of proteins. These changes in proteins may be associated with the expression of new biological activities which are not intrinsic characteristics of the proteins themselves. These biological effects include phlogistic activities in such structurally changed proteins; see J. H. Wissler in Proc. Immunosymposium Vienna 1973, "Gram-negative Bacterial Infections and Mode of Endotoxin Actions; Pathophysiological, Immunological and Clinical Aspects" (B. Urbaschek, R. Urbaschek and E. Neter (eds.), Springer-Verlag, Vienna 1975, p. 91–105.

The existence of cellular mediators which may cause directional growth of blood vessels, in a biologically specific manner and free of side effects, has not been known or shown so far.

Chemotropism of blood vessel sprout is measured by chemotropic neovascularization of the cornea of rabbits or guinea pigs after focal administration of the substance to be investigated. The rabbit cornea is a physiologically avascular, transparent tissue. Another assay to test blood vessel growth, vascularization of tissue and morphogenesis of blood vessel patterns is the chorioallantoic membrane assay by which the sprouting and formation of blood vessel patters in chicken embryos is investigated. A third assay investigates the mitogenic activity of the substance assayed on cultured endothelial cells.

It is therefore a primary object of this invention to provide a new class of cellular angiotropins from leukocytes.

It is another object of this invention to provide a new class of cellular angiotropins from leukocytes in highly purified, molecularly homogenous form.

It is another object of this invention to provide a new class of cellular angiotropins from leukocytes in physical quantities for practical use.

It is another object of this invention to provide a new class of angiotropins from leukocytes, which represent biologically specific, active and naturally acting mediators of angiogenesis reactions.

It is another object of this invention to provide a new class of chemorecruitins from leukocytes, which are capable of specifically inducing the directional growth of blood vessel sprouts in vivo.

It is still another object of this invention to provide a process for producing and obtaining a new class of angiotropins from leukocytes in a highly purified, molecularly homogenous form and in physical quantities for practical use.

It is still another object of this invention to provide a pharmaceutical composition for specifically inducing the directional growth of blood vessels.

These and other objects and advantages of the present invention will be evident from the following description of the invention.

SUMMARY OF THE INVENTION

The subject matter of the invention are angiotropins of leukocytes and inflamed tissues, characterized by the following properties:

(a) biological activities in vivo and in vitro:
specific chemotropic action on blood vessels in vivo;
induction of directional growth (chemotropism) of blood vessels along its concentration gradient;
during vessel sprouting, tips of growing vessel capillaries have increased capillary permeability (FIG. 1);
induction of neovascularization of tissues by directional in-growth of blood vessels (FIGS. 1 and 2);
they are substantially free of other biological effects;

(b) physico-chemical properties:
electrophoretic migration in acrylamide matrices at a pH of 7.40 is anodic;
soluble in aqueous media including in 20% ethanol at a pH value of at least 4.0 to 10;
constant temperature coefficient of solubility in ammonium sulfate solutions between $-10°$ C. and $+50°$ C.;
they absorb reversibly in structure and biological activity on anion and cation exchangers, calcium phosphate gel and hydroxyapatite and can be subjected in native form to volume partition chromatography.

The angiotropins derived from leukocytes and inflamed tissue have been evaluated and obtained in highly purified form for the first time by this invention. The angiotropins of the invention are further characterized by the fact that they are substantially free of other biological effects. More particularly the angiotropins of the invention do not show:

mobilization of adult or juvenile leukocytes (no leucocytosis or leftward shift reaction);
direct capillary permeability-enhancing activity in the skin test;
spasmogenic effects on smooth muscles;
spasmogenic effects on striated muscles;
endotoxin contents and endotoxin-like or similar activities;
chemical attraction effects (chemotaxis) of leukocytes in vitro;
positive or negative chemokinetic effects on leukocytes in vitro;
phagocytosis-stimulating effects on leukocytes in vitro;
apparent shock or other systemically detrimental effects of the immediate or protracted type on the intact organism of mammals in vivo;
significant pyrogenic effects in vivo;
lysis effects in vitro on erythrocytes, thrombocytes and leukocytes;
mitogenic effects on leukocytes in vitro;
chalone activity on leukocytes in vitro.

DETAILED DESCRIPTION OF THE INVENTION

The angiotropins of the invention have typical protein properties and protein reactions (folin and biuret reactions). Their melting point is approximately at 200° C. (decomposition in an air and oxygen-free atmosphere).

The angiotropins of the invention are cell-derived inflammatory mediators with topobiochemically and biologically specific activity. Their biological task is the induction and regulation of the directional growth of blood vessels and the morphogenesis of blood vessel patterns in vivo. This can lead to the neovascularization of tissue. The angiotropins are no normal and independent components of the blood and of blood-serum. They are formed together with a variety of other hormones and mediators in vitro by the culture of leukocytes or in vivo in the course of the accumulation of leukocytes at the reaction site of inflammation.

The angiotropins of the invention differ in all their biological, chemical and physico-chemical properties from structural and functional properties of bacterial endotoxins. The other molecular properties of the angiotropins of the invention, especially their low activity threshold, also intimate the similarity of these inflammatory mediators with hormones. The active threshold doses are in the fmol range. A value for $LD_{50}$ cannot be measured, since no lethal effects have been observed even with doses 10,000 times the amount of the physiologically active threshold dose.

Figure 3:
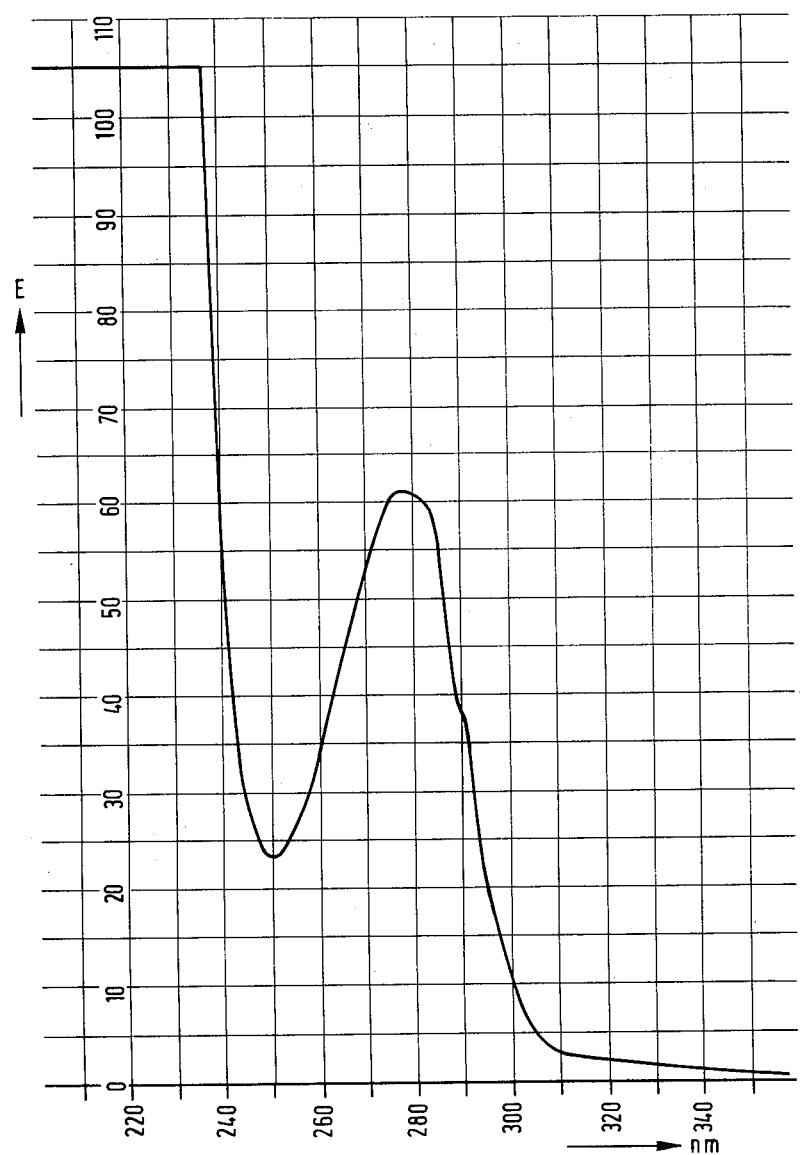

The angiotropin substances of the invention are exemplified below by a monocyte-derived angiotropin which, accordingly, is called "monocyto-angiotropin" (MAT) and by a granulocyte-derived angiotropin which, accordingly, is termed "granulocyto-angiotropin" (GAT). This nomenclature is in line with that suggested by hormone nomenclature commissions: Firstly, new substances are termed in sequence by the cell type which forms them; secondly by the cell or tissue type on which they act, i.e. the target cell; and thirdly, by the action itself;

Apart from and in in addition to the above-mentioned properties which angiotropins have in common, MAT has the following (special) properties:
effective threshold dose in vivo: <2,5 fmol
molecular weight of the native protein (primary structure); approximately 4,500 dalton;
no protein quaternary structure in the form of physically bound peptide subunits: each of the native proteins consists of only one peptide unit
soluble in an ammonium sulfate solution at 90% saturation (3.6 mol/l);
it contains, amongst others, the amino acids tyrosine, phenylalanine, alanine, glycine, valine, cysteine and aspartic acid;
absorption spectrum (UV, visible and near IR-range) as given in FIG. 3;
extinction coefficients according to the following Table I:

TABLE I

| wave length, nm | $E_1$ $_{mg/ml,\ 1\ cm\ (H_2O,\ 20°\ C.)}$ ± 6% |
|---|---|
| 250 (min) | 0.18 |
| 260 | 0.28 |
| 277 (max) | 0.49 |
| 280 | 0.48 |
| 290 | 0.30 |
| 400–1000 | 0 |
| $E_{280}/E_{260}$ | 1.71 |

Figure 4:
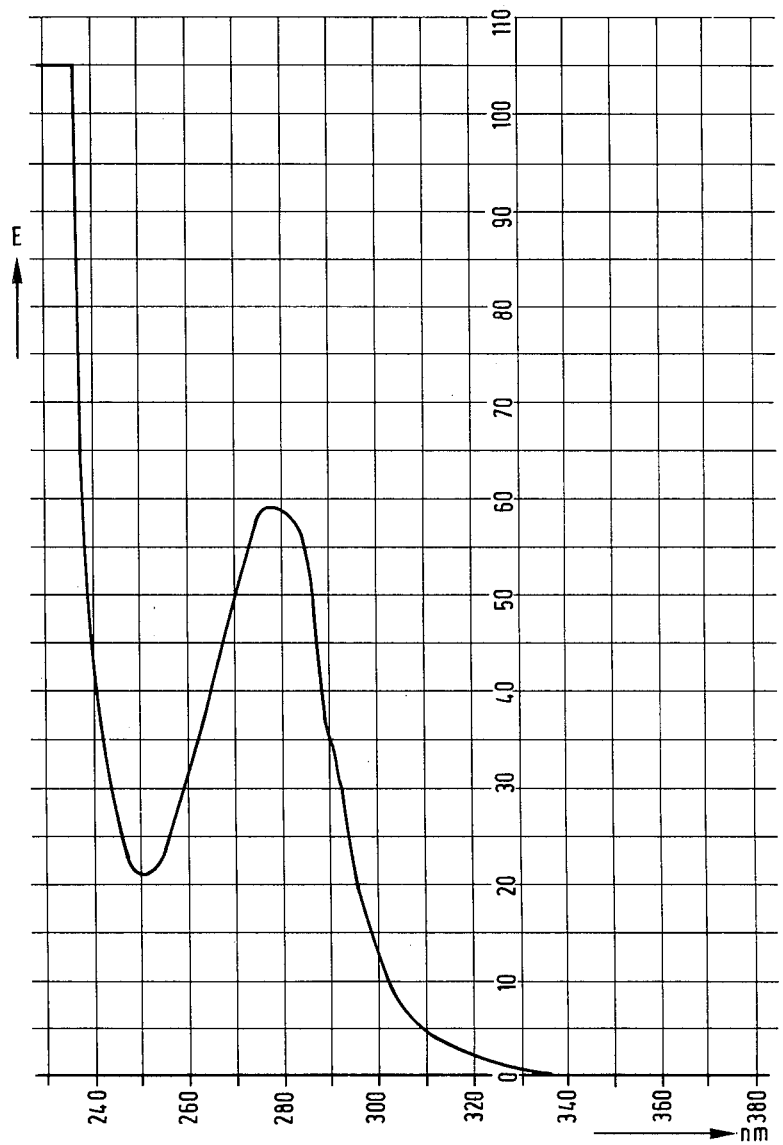

Apart from and in addition to the above-mentioned properties which angiotropins have in common, GAT has the following (special) properties:
effective threshold dose in vivo: <50 fmol
molecular weight of the native protein (primary structure): approximately 35,000 dalton;
insoluble in an ammonium sulfate solution at 35% saturation (1.4 mol/l);
it contains, amongst others the amino acids tyrosine, phenylalanine, alanine, glycine, valine, cysteine, aspartic acid, proline and arginine;
absorption spectrum (UV, visible and near IR-range) according to FIG. 4;
extinction coefficient according to the following Table II:

TABLE II

| wave length, nm | $E_1$ $_{mg/ml,\ 1\ cm\ (H_2O,\ 20°\ C.)}$ + 6% |
|---|---|
| 250 (min) | 0.21 |
| 260 | 0.30 |
| 277 (max) | 0.59 |
| 280 | 0.58 |
| 290 | 0.35 |
| 400–1000 | 0 |
| $E_{280}/E_{260}$ | 1.93 |

Up to non-physiological concentrations of 10 μmol/l the angiotropins of the invention have neither chemotactic nor chemokinetic, nor phagocytosis or mitosis-stimulating nor chalone activities on neutrophil, easionophil and mononuclear leukocytes of man, rabbit, pig, dog, guinea pig or rat. Furthermore, they have no spasmogenic activity on smooth muscles of the guinea pig ileum and no capillary permeability enhancing activity in the guinea pig skin test using Evans blue as intravenously applied dye marker. Finally, they have no apparent shock and other systemically detrimental activity of the immediate or protracted type in guinea pigs or rabbits, even when intravenously applied as one bolus up to a 10,000 fold dose of the biologically active (blood vessel sprout-inducing) threshold. Furthermore, angiotropins have no other apparent systemic biological activity when intravenously applied in a single high dose of about 10 nmol/kg to guinea pigs or rabbits. Moreover, they have no pyrogenic activity in rabbits, as shown by the standardized method by measurement of rectal temperature according to Europ. Pharmacopoeia, vol. II (1975), p. 56 to 59.

Figure 1:
Figure 2:

FIGS. 1, 2 and 6 show the induction of neovascularization of the cornea of the rabbit by directional growth of blood vessels following focal intracorneal administration of angiotropins. FIGS. 1 and 2 show the aciton of highly purified MAT and GAT protein substances which have been prepared by leukocyte cultures after a more than 100,000 fold purification from the crude supernatant culture solution. FIG. 6 shows the action of highly purified MAT protein substance prepared from inflamed (infarcted) heart muscle tissue.

FIGS. 3 and 4 show the UV absorption spectra of the angiotropins MAT and GAT in water at 20° C. and an extinction scale (0–100) E=0–2 at a light path d=1 cm.

Figure 5A:
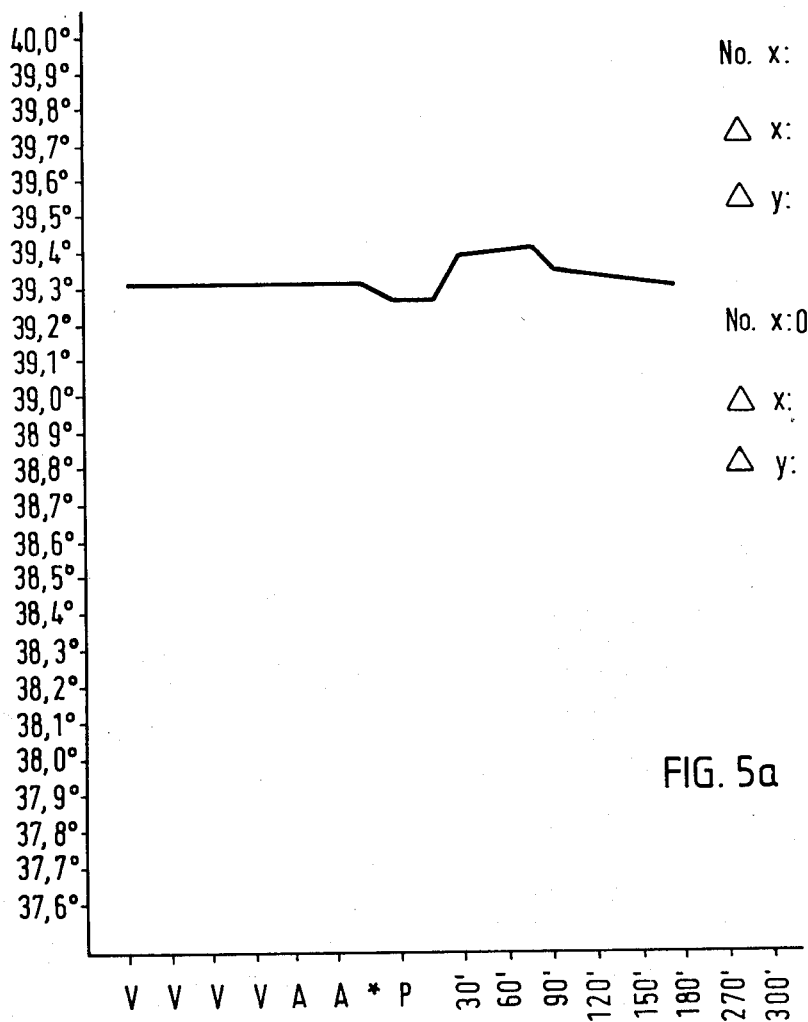
Figure 5B:
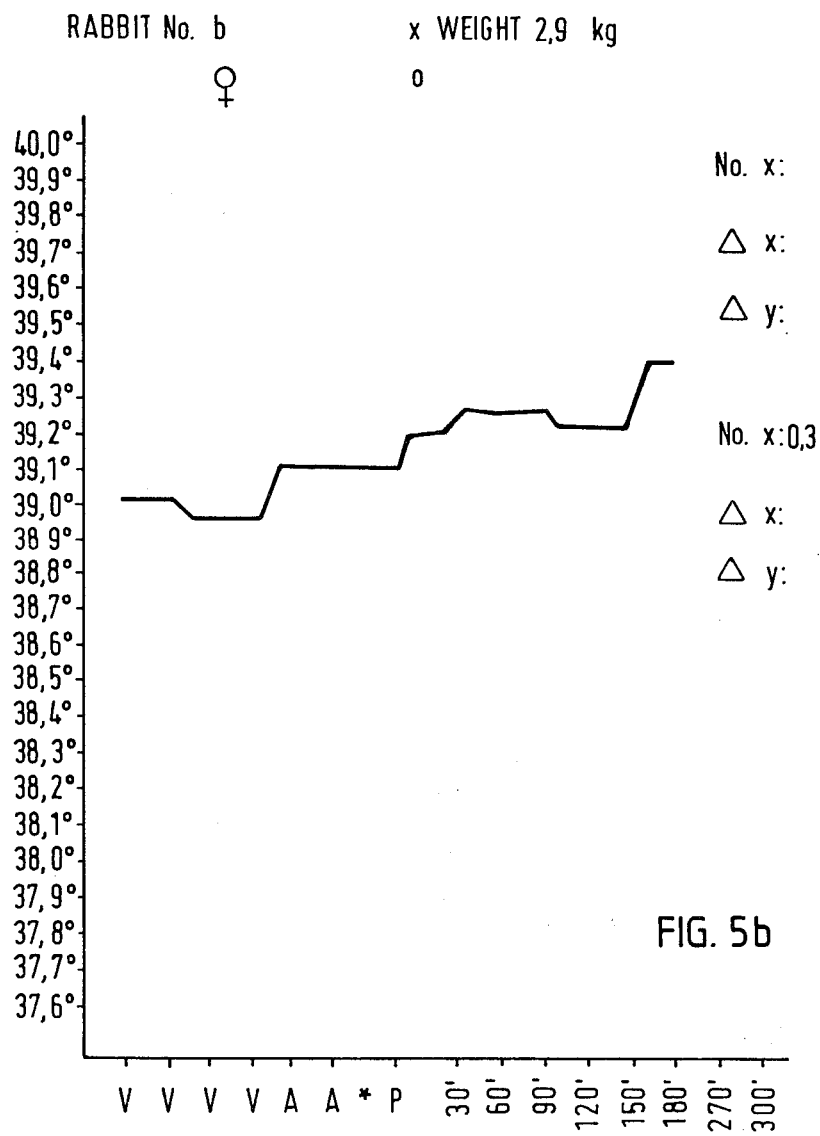
Figure 5C:
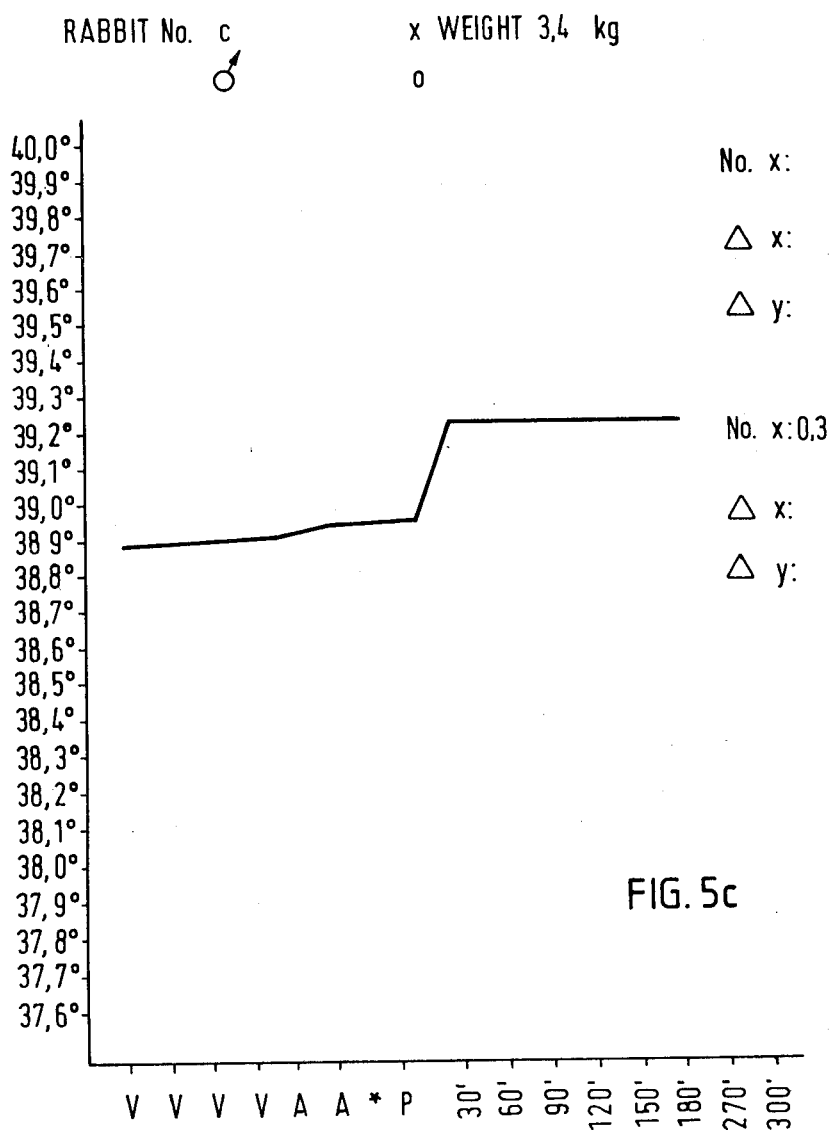

In FIG. 5 a standard-pyrogen assay is represented according to Europ. Pharmacopoeia, vol. II (1975): Rectal temperature of 3 rabbits having an average weight of 3 kg is measured prior (V,A), during (*) and 30–180 minutes after (P) intravenous application of 5 μm MAT (about 0.3 nmol MAT/kg animal) in 1 ml 0.9 (w/v)% physiological saline. This corresponds to about the 300,000-fold (focal) amount of the biologically (angiotropically) active threshold.

The 1975 edition of the European Pharmaceopoeia, the British (1973) and the American (USP) (1975) Standards allow the designation "pyrogen-free" to be applied to preparations for which the sum of the fluctuations of the rectal temperature in a total of three experimental rabbits does not exceed the value of 2.6° C. and, in particular, is below 1.15° C. The experimental results given in FIG. 5 fullfills these criteria. According to these definitions, the MAT-preparation is pyrogen-free and without febrile activity. This also applies to the highly purified GAT-preparation. This extremely sensitive criterion for contamination of proteins with bacterial endotoxins and other ubiquitous pyrogens demonstrates the great efficacy of the process of the purification of the cellular angiotropins of the invention. It is an obvious parameter for the biolgocial specificity of the angiotropins.

The leukocyte-derived angiotropins prepared and obtained according to the invention are valuable, endogenous and active protein substances. They can be used for influencing the vascular state of tissue, lungs, or in general, in tissue regeneration processes, such as reproductive cycles, embryogenesis and transplantations. A further possible mode of application is the preparation of inhibitors for suppression of undesired angiogenesis and neovascularization reactions in tissue. These pathological angiogenesis reactions are known and appear in the course of various processes, such as in tuberculosis, diabetes, tumors, reproductive cycles and tissue graft reactions. Thus it is well known that medical care of undesired pathological vascularization processes of normally avascular ocular tissues is hardly achieved. For the latter proposed mode of application, the use of angiotropins is also possible for the production of anti-angiotropin immunoglobulins and their fractions.

The angiotropins of the invention are locally applied alone or in admixture in the form of usual pharmaceutical compositions to mammals, for instance to man in amounts higher than 1 fmol or in concentrations of $>10$ pmol/l.

Another subject matter of the invention is a process for the biotechnical preparation and isolation of angiotropins from leukocytes and from inflamed tissue sites. It is characterized in that either the leukocytes or the inflamed tissue are homogenized; or that leukocytes are cultured and the angiotropins formed or liberated are isolated from the homogenates or from the supernatant culture solution.

In principle, it is possible to prepare mediators from leukocytes directly without cell cultures. However, such a procedure is not economical: The leukocytes are destroyed by the process; the yields in mediators are low, since their synthesis and secretion is not stimulated prior to isolation; the mediators can be contaminated by intracellular structural constituents of leukocytes. Therefore, in the process of the invention, it is preferred to isolate the angiotropins from the supernatant solution of the leukocyte culture. In principle, the leukocytes can be cultured in any leukocyte-compatible medium.

For the culture of different cell types, such as bone marrow cells, heart muscle cells or leukocytes, different culture media are known. These media normally are aqueous solutions which contain numerous different compounds. Main constituents of these culture media are salts, sugars and metabolites, amino acids and derivatives, nucleosides, vitamins, vitaminoids, coenzymes, steroids and other additives, such as tensides, heavy metal salts and indicator dyes. Special examples of known culture media are named "HAM", "MEDIUM 199" and "NCTC", see H. J. Morton, In Vitro 6 (1970) p. 89 to 108.

When culturing cells for more than one hour, as in the case of leukocytes, mostly serum (e.g. fetal calf serum or horse serum) is added to the culture medium. The serum constituents are said to be favourable for the maintenance of cellular function. However, if the serum-containing culture solution is to be subjected to processes for isolating proteins (mediators) which are formed by culturing cells, the preparation of trace protein products is difficult for reasons of the multiplicity of compounds making up the complex mixture of serum added to the culture. In addition, under such conditions, upon addition of serum to a cell culture medium, it is difficult if not at all impossible to recognize the origin of the mediators: It is then an open question whether or not a distinct mediator is of humoral (serum) or cellular (leukocyte) origin and from which species this mediator stems. Thus, the mediator may be derived from the species whose cells have been cultured; or, alternatively, it may be derived from the species from which the added (mostly heterologous) serum stems.

Besides serum-containing culture media, serum-free, synthetic media are also known; see H. J. Morton, loc. cit; I. Hayashi and G. H. Sato, Nature 259 (1976) p. 132-134; N. N. Iscove and F. Melchers, J. Exp. Med. 147 (1978) p. 923-933.

However, these known media likewise have drawbacks for both the culture of cells and for the preparation of the mediators formed from the culture supernatant. The tensides, heavy metal salts and/or dyes contained therein may damage or irreversibly contaminate the trace mediator proteins.

On the other hand, such known serum-free media are devoid of essential constituents which are necessary for maintaining the structural and functional viability of leukocytes. Therefore, none of the culture media known so far can be suitably used for the culture of leukocytes and the biotechnical preparation of cellular trace components, such as angiotropins.

For the culture of leukocytes, a new, fully synthetic chemically defined culture medium is preferably used. It provides favourable conditions for cell culture and facilitates the preparation and isolation of the cellular angiotropin proteins from the culture supernatant.

The fully synthetic, chemically defined cell culture medium preferably used in this invention contains the normal groups of compounds, such as salts, sugars, polyols, uronic acids, and derivatives, amino acids and derivatives, nucleosides and nucleoside bases, vitamins, vitaminoids, phytyl derivatives, coenzymes and steroids in aqueous solution. It is characterized in that it additionally contains one or a mixture of several compounds which so far have not been considered for use in cell culture media. These are especially valuable for expression of the life functions, for the proliferation of leukocytes and for promoting their capability to produce mediators. These substances include unsaturated fatty acids, flavanoids, ubiquinone, vitamin U, mevalolactone and L-carnosine.

In prolonged leukocyte culturing, the cell culture medium is preferably used without addition of serum. Instead, it contains at least one defined protein.

In further preferred embodiments of the invention, the synthetic, serum-free cell culture medium used in this invention may contain additional compounds, e.g. polyhydroxy compounds and sugars, amino acids, nucleosides, anionic compounds and/or vitamins which are not common in the known culture media. These compounds are useful in culturing leukocytes. The constituents in the culture medium used in this invention are equilibrated in their ratios so that their concentrations mainly correspond to the natural concentration ranges of the plasma; see Ciba-Geigy AG (editor) (1969) in Documenta Geigy, Wissenschaftliche Tabellen seventh edition, Geigy S.A. Basle.

Preferably, the cell culture medium is free of tensides, heavy metal salts and dye indicators which can damage the cells and may have a detrimental effect on the isolation of the desired cell products.

The exact composition and the properties of the new cell culture medium are described in the Patent Application Ser. No. 358,045 filed simultaneously on the basis of West German Patent Application No. P 31 10 559.9.

The cell culture medium with the composition given in Table III below is especially preferred in the process of the invention for culturing leukocytes.

The medium is prepared with water of ASTM-1-quality; see ASTM D-1193-70 Standard Specification for Reagent Water 1970; Annual Book of ASTM-Standards, Easton, Maryland, ASTM 1970. In addition, it is freed from possible endotoxin-contaminations by ultrafiltration on tenside-free membranes with an exclusion limit of 10,000 dalton. The resulting medium is sterilized by filtration on tenside-free membranes with a pore size of 0.2 $\mu$m.

cyte types are cultured. The preparation and culture of leukocytes must be performed under sterile conditions. Culturing is performed for a period sufficiently long to obtain a satisfactory medator level. A suitable period of time is 10 to 50 hours. Shorter periods result in lower mediator yields and the process is thus not economical. On the other hand, the medium is used up after a culture period of 50 hours and the cells begin to die. An increase of the yield can therefore not be obtained in this case, except in the case of subculturing of cells and renewal of the culture medium.

The leukocytes are cultured at a temperature of about 30° to 42° C., preferably at about 37° C. At lower temperatures the culture process is not satisfactory, while at temperatures of above 42° C. the leukocytes are damaged.

Culturing is carried out at a concentration of about $10^6$ to $5 \times 10^8$ cells/ml, preferably $10^7$ to $10^8$ cells/ml. At lower cell concentrations the mediator yield per volume unit of the culture solution is too low. With too large culture volumes, the process is not economical. At cell concentrations of above $5 \times 10^8$ cells/ml, nutrition

TABLE III

| No. | Component | mol/l | No. | Component | mol/l |
|---|---|---|---|---|---|
| 1 | Disodium hydrogenphosphate | 0.8 m | 48 | L-Alanine | 0.2 m |
| | | | 49 | L-Arginine | 0.1 m |
| 2 | Potassium dihydrogenphosphate | 0.2 m | 50 | D,L-Carnithine chloride (BT) | 50.0$\mu$ |
| 3 | Potassium chloride | 5.0 m | 51 | L-Carnosine | 5.0$\mu$ |
| 4 | Sodium chloride | 120.0 m | 52 | L-Cysteine | 0.2 m |
| 5 | Sodium sulfate | 0.2 m | 53 | L-Glutathione reduced | 3.0$\mu$ |
| 6 | D-Glucose | 5.0 m | 54 | Glycine | 0.2 m |
| 7 | L-Ascorbic acid (C) | 0.2 m | 55 | L-Histidine | 0.1 m |
| 8 | Choline chloride | 50.0$\mu$ | 56 | L-Hydroxyproline | 10.0$\mu$ |
| 9 | 2-Deoxy-D-ribose | 5.0$\mu$ | 57 | L-Lysine-HCl | 0.2 m |
| 10 | D-Galactose | 0.5 m | 58 | L-Methionine | 0.1 m |
| 11 | D-Glucurono-$\gamma$-lactone | 0.1 m | 59 | D,L-Mevalolactone | 5.0$\mu$ |
| 12 | Glycerol | 50.0$\mu$ | 60 | Nicotinic acid amide | 20.0$\mu$ |
| 13 | Myo-inositol | 0.5 m | 61 | L-Ornithine-HCl | 50.0$\mu$ |
| 14 | Sodium acetate | 0.2 m | 62 | D-Ca-pantothenate (B5) | 5.0$\mu$ |
| 15 | Sodium citrate | 50.0$\mu$ | 63 | L-Proline | 0.1 m |
| 16 | Sodium pyruvate | 0.1 m | 64 | Pyridoxal-HCl | 5.0$\mu$ |
| 17 | D-Ribose | 20.0$\mu$ | 65 | Pyridoxine-HCl (B6) | 2.0$\mu$ |
| 18 | Succinic acid | 0.1 m | 66 | Sarcosine | 50.0$\mu$ |
| 19 | Xylitol | 10.0$\mu$ | 67 | L-Serine | 0.1 m |
| 20 | D-Xylose | 20.0$\mu$ | 68 | Taurine | 0.1 m |
| 21 | Calcium chloride | 2.0 m | 69 | Thiamine-HCl (B1) | 5.0$\mu$ |
| 22 | Magnesium chloride | 1.0 m | 70 | L-Threonine | 0.2 m |
| 23 | Sodium hydrogencarbonate | 10.0 m | 71 | Vitamin B 12 | 0.5$\mu$ |
| | | | 72 | Vitamin U | 1.0$\mu$ |
| 24 | Serum albumin (human) | 7.7$\mu$ | 73 | Adenine | 50.0$\mu$ |
| 25 | L-Asparagine | 0.1 m | 74 | Folic acid (Bc) | 5.0$\mu$ |
| 26 | L-Glutamine | 1.0 m | 75 | Guanine | 5.0$\mu$ |
| 27 | Adenosine | 50.0$\mu$ | 76 | Guanosine | 20.0$\mu$ |
| 28 | 4-Aminobenzoic acid | 2.0$\mu$ | 77 | Hypoxanthine | 5.0$\mu$ |
| 29 | L-Aspartic acid | 0.1 m | 78 | Rutin (Vitamin P) | 5.0$\mu$ |
| 30 | D-Biotine (Vitamin H) | 1.0$\mu$ | 79 | Xanthine | 5.0$\mu$ |
| 31 | Cytidine | 50.0$\mu$ | 80 | Ethanol (60 $\mu$l/l) | 1.0 m |
| 32 | L-Glutamic acid | 0.1 m | 81 | Cholesterol | 1.0$\mu$ |
| 33 | L-Isoleucine | 0.2 m | 82 | Ergocalciferol (D2) | 0.5$\mu$ |
| 34 | 5-Methylcytosine | 5.0$\mu$ | 83 | D,L-$\gamma$-Lipoic acid | 2.0$\mu$ |
| 35 | L-Phenylalanine | 0.1 m | 84 | Menadione (K3) | 0.2$\mu$ |
| 36 | Riboflavine (B2) | 1.0$\mu$ | 85 | D,L-$\gamma$-Tocopherol acetate (E) | 1.0$\mu$ |
| 37 | Thymine (5-methyluracil) | 5.0$\mu$ | | | |
| 38 | L-Tryptophane | 50.0$\mu$ | 86 | Coenzyme Q 10 ubiquinone 50 | 0.1$\mu$ |
| 39 | L-Tyrosine | 0.1 m | | | |
| 40 | Uracil | 5.0$\mu$ | 87 | 3-Phytylmenadione (K1) | 0.2$\mu$ |
| 41 | Uridine | 20.0$\mu$ | 88 | Retinol acetate (A) | 1.0$\mu$ |
| 42 | L-Leucine | 0.2 m | 89 | Linolenic acid (F) | 5.0$\mu$ |
| 43 | L-Valine | 0.2 m | 90 | Linoleic acid (F) | 1.0$\mu$ |
| 44 | Thymidine | 20.0$\mu$ | 91 | Oleic acid | 5.0$\mu$ |
| 45 | Water | 55.4 | 92 | Penicillin G | 80.0$\mu$ |
| 46 | Hydrogen ions (pH 7.1) | 79.4 n | 93 | Streptomycin | 80.0$\mu$ |
| 47 | Oxygen (air saturation) | 0.2 m | 94 | Activator(s) (CON A) | 50.0 n |

Dependent on the type of desired product, either mixed populations of leukocytes or homogenous leukoof the cells in the medium becomes rapidly inefficient.

Culturing can be carried out in normal atmosphere. Preferably increased carbon dioxide partial pressure is maintained during culturing. This pressure can amount to about 10 vol%. 2 vol% are preferred. The oxygen supply to the culture is of great importance. Oxygen can be supplied e.g. by bubbling air through the culture. To avoid contamination of the culture, the air is preferably sterilized and heat-decontaminated, i.e. it is freed of endotoxins and other organic constituents. The cell suspension is stirred or agitated during culturing.

Certain types of the inventive angiotropins are already obtained in satisfactory yields by normal culture of leukocytes or certain leukocyte types. The GAT, for instance, is obtained in high yields by culturing mixed populations of leukocytes or homogenous populations of granulocytes under the above-indicated conditions.

Other types of angiotropins of the invention are however only formed in small amounts by normal culture of leukocytes or certain leukocyte types. This applies for instance to the angiotropin of mononuclear cells, (MAT).

To produce it in higher yields, it is necessary to stimulate the cells in culture to mitosis. Possible mitosis-inducing influences are the addition of polyvalent mitogens, endotoxin-mitogens and immune reactions on the cell surface of sensitized cells. Examples of suitable mitogens are lectins, in particular those of *Canavalia ensiformis* (Concanavalin A=CON). The mitosis-inducing factor CON is added as a solution to the culture medium.

To terminate culturing, the leukocytes are centrifuged from the supernatant culture solution which is subsequently processed for the resulting angiotropins. To avoid damaging the cells and thus contamination of the culture solution with cell particles, the culture is centrifuged at relatively low speed, i.e. at about 300 to 400×g. After removal of the major part of the cells from the supernatant, it is expedient to centrifuge the latter again at a higher speed. In this way, the remaining floating particles are removed. The separated leukocytes can either be again subcultured, cryo-preserved or used for other biotechnical purposes.

The supernatant culture solution freed from the cells contains the secretion products of the cultured leukocytes. These include the angiotropins of the invention and a number of other proteins and other substances. Their concentration in the culture solution is approximately within the nanomolar range. Consequently, a yield of about 1 to 10 mg of a defined mediator requires a culture solution volume of about 1,000 l with respect to a 10% recovery after purification. As regards the number of cells to be used, it can be calculated that in view of the molecular efficiency of the cells, about $10^{14}$ leukocytes are necessary for obtaining a quantity of about 100 nmol proteins. This corresponds to about 1 mg of a mediator with the molecular weight of 10,000 dalton. This means that for the isolation of mediators in physical amounts about 50 kg of leukocytes are necessary for the culture. For reasons of availability, leukocytes of man, cow, horse, pig, sheep, dog, cat, rabbit, rat, mouse or guinea pig are preferred. The process described in the German unexamined patent publication DE-OS No. 30 09 126 is especially suitable for the preparation of large amounts of leukocytes; see also J. H. Wissler et al, Z. f. Physiol. Che. 361 (1980), p. 351 to 352.

Apart form leukocyte cultures, the angiotropins of the invention can also be obtained from inflamed tissue sites. There, they are formed by the accumulation of leukocytes in the course of inflammatory processes induced by tissue injuries. The inflamed tissue can be obtained in the usual manner and used for the preparation of the angiotropins. Inflamed tissues are homogenized in buffer solution and soluble constituents or exudates are separated from insoluble structural components by means of centrifugation.

Preferably, inflamed, infarcted heart muscle tissue is used which was formed by ligation of 24 hours of the left anterior descendent branch of the left coronary artery by a transfemural catheter technique. The leukocyte-containing inflamed heart muscle site is separated at 0° to 4° C. from the remaining non-infracted tissue.

As shown above, the preparation and isolation of the angiotropins of the invention requires the processing of a very large culture solution volume. Therefore, at the beginning of the purification process effective reduction of the solution volume to be processed is necessary. In addition to the small amounts of the proteins produced, the culture solution contains the mixture of the components of the medium. Preferably, in the first step of the purification process a separation of the formed proteins from the medium components with a concomitant reduction of the large volume of aqueous solution is achieved. This can be effected by selective salting-out precipitation of the proteins from the supernatant culture solution, for instance by adding a sulfate or a phosphate. In the following, the salting-out preciepitation of proteins is exemplified by adding ammonium sulfate to the culture solution.

By saturation of the supernatant culture solution with ammonium sulfate, a major portion of the proteins formed is precipitated together with serum albumin present as medium component. The proteins precipitated are recovered e.g. by centrigution. They are then separated into the individual components of the mixture as described below. Thereby, some angiotropins are obtained. On the other hand, some other angiotropins are salt-soluble and remain in the supernatant solution of the salting-out precipitation process. This supernatant also contains all soluble components of the medium. It is concentrated and the proteins obtained are processed in the manner described below.

If the protein-containing supernatant culture solution is saturated with ammonium sulfate, a major portion of proteins is precipitated. In this way, a protein mixture is obtained consisting of numerous different proteins. Their separation into the individual protein components is obviously laborious. Therefore, in a preferred embodiment of the inventive process the protein mixture of the supernatant culture solution is already separated into several fractions by the salting-out precipitation step. The separation into several crude protein fractions is possible, since groups of individual proteins precipitate at different ammonium sulfate concentrations. Preferably, in the process of the invention, ammonium sulfate is therefore added stepwise to the culture solution up to a specific degree of saturation. Each fraction contains a group of proteins, the solubility product of which corresponds to the range of salt saturation. Hence, in the process according to the invention a crude separation into groups of proteins can be achieved in this first step by suitable choice of the saturation limits.

For instance, the supernatant culture solution is first brought to a 35% saturation with ammonium sulfate. The protein precipitate obtained is separated off. The 35% saturation of the supernatant solution is then increased to 45% by further addition of ammonium sulfate. A protein precipitate is again formed which is separated off. Thereafter, the 45% salt-saturated supernatant solution is brought to a 90% ammonium sulfate saturation. The protein precipitate formed is again separated off. The supernatant solution of this precipitate is concentrated e.g. by dehydration dialysis or ultrafiltration.

The salting-out precipitation of proteins is preferably carried out at a temperature of about 0° to 10° C., especially of about 0° to 4° C. The subsequent purification steps are performed under the same conditions. The solutions used for the purification have a pH value of between 5 and 9, in particular between 6 and 8. In order to achieve a constant pH-value of the solution, a strong buffer, for instance 0.1 mol/l of phosphate buffer is preferably added prior to the salting-out precipitation. To maintain the redox potential of the proteins, cysteine is preferably added in an amount of 0.001 mol/l to all solutions throughout the process. The protein purification does not require sterile conditions.

After dissolution in a protein-compatible medium, the proteins obtained by salting-out precipitation can be directly subjected to purification and separation in the manner described below. The 90% salt-saturated supernatant of the last precipitation step is concentrated. For instance, by dehydration dialysis or ultrafiltration, all compounds having a molecular weight higher than about 300 to 500 dalton are obtained as a retentate fraction. They can also be further processed for purification of salt-soluble chemorecruitins.

The protein fractions obtained in the step described above contain the angiotropins of the invention in admixture with numerous foreign proteins, e.g. other secreted proteins, in part serum albumins and in part CON. These foreign proteins form the major part of the constituents of this mixture. The angiotropins must be further purified by a sequence of further purification steps. Foreign proteins must be removed to avoid interference with the molecular-biological specifity of angiotropins. In addition, angiotropins themselves form a class of protein compounds which must be separated into individual, specifically acting structures.

In general, purification processes for proteins and other natural substances comprise sequences of combined separation techniques. Subtle differences in molecular size, charge, form, structure stability and nature of molecular surfaces between the desired natural substance and the accompanying inactive foreign materials are used in such purification steps for their separation. Accordingly, a large number of combinations of various modifications of preparation techniques can be devised for the purification of a protein. The nature and the conditions of the preparation steps used, but also their sequential combination, are of paramount significance for operational properties, technical practicability, possibility of optional automatization and for the economical performance of a purification process and also for the yield and molecular quality of a natural product investigated. Particular attention has to be given to the optimum form of separation steps and on their ingenious combination into a purification sequence within the framework of structural and functional stability and other molecular parameters of the substance under investigation. This implies that the use of identical or similar separation principles (molecular sieve filtration, dialysis, ion exchange absorption, etc.)—however in a different combination—can be of specific and paramount importance for the practice and economical performance of the purification process as well as for the yield and quality of the product obtained. In some cases, the use or ommission of a single technique (.e.g hydroxyapaptite chromatography, zone precipitation chromatography, etc.) at a certain point in the purification sequence or within a partial sequence, is of decisive significance for the yield and quality of the desired natural product as well as for the practice and economical performance of the purification process. These general relationships and basic principles inherent to the purification processes of natural products are clearly illustrated e.g. by some well known facts. Thus, within an economically and technically operable process for the purification of a natural product, initial dialysis, ultrafiltration or lyophilization steps are not recommended prior to reduction of original volumes of crude starting extracts by a factor of at least 500 to 1000 through other techniques.

For the purification of the individual protein fractions, a plurality of purification steps so far known in biochemistry can be used. Examples of such purification steps are: Preparative and analytical molecular sieve chromatography, anion and cation exchange chromatography and bath absorption techniques, chromatography on hydroxyapatite, zone precipitation chromatography and recycling or cascade molecular sieve filtration.

It is possible to remove a considerable amount of accompanying foreign proteins from angiotropins by only one performance of these purification methods. However, proteins contained in the fractions tend to adhere together very strongly. Therefore, for example, inspite of different molecular weights of proteins, by molecular sieve filtration, no complete (ideal) separation of protein polyelectrolytes according to their exact molecular weight is obtained immediately. Hence it is necessary to perform at least two of the mentioned separation processes in sequence. A particularly preferred embodiment of the process in accordance with the invention uses three of the mentioned purification steps in sequence for the purification of angiotropin activity from the protein fractions.

All combinations of the mentioned separation steps constitute objects of the invention. It is evident, that certain sequences of separation steps are of less advantage than other combinations. Thus, for example, it is imperative to perform a preparative molecular sieve filtration before an analytical molecular sieve filtration: In reverse order of performance, difficulties in handling, economic efficiency and yield are obvious.

Molecular sieve filtration achieves separation of proteins according to their molecular weights. Since the bulk of the foreign proteins have molecular weights different from those of angiotropins they can be separated off in this manner. A hydrophilic water-swelling molecular sieve as matrix is used for separation of the proteins by molecular weight. Examples of suitable molecular sieve matrices are dextrans cross-linked with epichlorohydrin (Sephadex), agaroses cross-linked with acrylamides (Ultrogels), and three-dimensionally cross-linked acrylamides (Biogels). The exclusion limits of the matrices used are higher than the separation limits.

If several separation steps are used, the molecular sieve filtration is preferably carried out as one of the first separation steps. Depending on the length-to-diameter ratio of the column used and the particle diameter of the gel matrix, molecular sieve filtration is termed "preparative" or "analytical". A molecular sieve filtration is "preparative" when the chromatography is performed on columns with a length-to-diameter ratio of up to 10:1 and a charge of the column of up to ⅓ of its capacity in terms of the total separation volume of the matrix. "Analytical" molecular sieve filtration means a length-to-diameter ratio larger than 10:1, and preferably about 50:1, and a maximum charge of the column of up to 3% of its capacity.

In preparative molecular sieve chromatography, gel matrices with the largest possible particle size are used for maximum flow-through rates of mostly viscous protein solutions applied at reasonably low pressures. In analytical molecular sieve filtration the particle size ranges of the gel matrix are selected as small as possible, to obtain a maximum number of theoretical plates, a flow rate of the mobile phase in the range of 2 to 4 cm/h combined with a pressure which is limited to technical and safety aspects. These parameters are dependent on the structure of the gel matrix and may vary from gel to gel.

If several preparative molecular sieve filtrations are performed in sequence, graduated separation limits can be selected. This can be followed by an analytical molecular sieve filtration with correspondingly graduated separation limits. The exclusion limit of the gel used must in all cases be higher than about 10,000 dalton to allow a volume distribution of angiotropins between the stationary gel matrix phase and the mobile aqueous buffer phase.

The "exclusion limit" is a hydrodynamic parameter of a dissolved particle, which corresponds to the pore size of the gel matrix. Particles with a greater hydrodynamic parameter cannot penetrate the gel matrix (volume distribution coefficient $K_D=0$). The "separation limit" refers to a hydrodynamic parameter which has been chosen for the separation of dissolved particles from others and which has a value of between the volume distribution coefficient $K_D=0$ and $K_D=1$.

For molecular sieve filtration, the proteins are applied to the molecular sieve after dissolution in a protein-compatible liquid. A special example of a suitable solvent is 0.003 mol/l sodium-potassium phosphate solution containing 0.3 mol/l NaCl and 0.001 mol/l cysteine and having a pH of 7.4. After filtration, the angiotropin-containing fractions are concentrated in the manner described below and optionally subjected to a further purification step.

Examples of suitable anion exchangers are dextran matrices cross-linked with epichlorohydrin (Sephadex) or cellulose matrices carrying functional groups with anion exchanger capacity. These exchangers can be regenerated for repeated further use. It is preferable to use a weak anion exchanger in the Cl$^-$ form such as DEAE-Sephadex A-50, pre-swollen and equilibrated in a buffer. Swelling and equilibration is preferably carried out at a pH of 8 to 10. A special example of such a buffer solution is 0.01 mol/l tris-HCl containing 0.04 mol/l NaCl and 0.001 mol/l cysteine and having a pH value of 8.0.

The anion exchanger is added to the protein fraction in an amount sufficient for complete adsorption of the angiotropins and of the other positively adsorbing accompanying proteins. Two volume parts of swollen anion exchanger per volume of concentrated protein solution are normally sufficient. The reaction can be carried out either as chromatographic process or as an easy and fast batch adsorption technique. In the latter case, the supernatant liquid containing negatively adsorbed proteins is separated from the anion exchanger which is charged with the positively adsorbed angiotropins or other proteins, e.g. by filtration in a chromatographic column, by decantation or centrifugation. The charged anion exchanger is freed from adhering negatively adsorbing compounds by washing with water or a salt solution having a maximum ionic strength equivalent to 0.04 mol/l NaCl, preferably at a pH of 8 to 10.

The maximum preferred temperature is about 15° C. A special example of salt solution suitable for the washing-out process is the said tris-HCl buffer of pH 8.0.

The anion exchanger on which angiotropins and other proteins are adsorbed and which is freed from the negatively adsorbed compounds is eluted with a protein-compatible aqueous salt solution having an ionic strength higher than 0.04 mol/l NaCl and a pH of between 4.0 and 10.0. A salt solution of high ionic strength and a pH of between 5.0 and 7.0 is preferably used. A special example of such a salt solution is a 2.0 mol/l NaCl solution buffered to a pH of 6.5 with 0.01 mol/l piperazine-HCl and containing 0.001 mol/l cysteine.

If the anion exchange reaction is carried out as a chromatographic process, elution of the angiotropins and other positively adsorbed proteins can also be done by a linear NaCl concentration gradient.

Examples of cation exchange matrices suitable for the purification of the protein fraction are dextrans cross-linked with epichlorohydrin (Sephadex) or cellulose matrices carrying functional groups with cation exchange capacity. These can be readily regenerated after use and employed again. It is preferable to use a weakly acidic cation exchanger such as CM-Sephadex C-50 having Na$^+$ as mobile counter-ion, and to perform the exchange reaction at a pH between 4 and 6. To facilitate the charge process and to approach more ideal equilibria conditions prior to treatment with the cation exchanger the protein fractions should be diluted with a protein-compatible salt solution having a maximum ionic strength equivalent to 0.04 mol/l NaCl. This salt solution can be used at the same time to adjust the pH. A special example of a salt solution for this purpose is a 0.001 mol/l potassium phosphate-acetate buffer containing 0.04 mol/l NaCl and 0.001 mol/l cysteine and having a pH of 4 to 6. This cation-exchange reaction may be performed as a chromatographic process, or technically easier, as a batch process.

The swollen cation exchanger is added to the protein fraction in a quantity sufficient to adsorb it. As a rule, about 2 volume parts of swollen ion exchanger per volume part of protein solution is sufficient for this purpose. The supernatant is then separated from the cation exchanger charged with proteins, for example by decantation or centrifugation. The charged cation exchanger is freed from adhering, negatively adsorbed compounds by washing with water or a salt solution, having a maximum ionic strength equivalent to 0.04 mol/l NaCl. Preferably a pH of about 4 to 6 and a maximum temperature of about 15° C. is used. A special example of a salt solution suitable for the washing out process is the mentioned potassium phosphate-acetate buffer having a pH of 5.0.

The washed protein-charged cation exchanger is now eluted with a protein-compatible aqueous salt solution. A salt solution of high ionic strength with a pH of about 4 to 10 is preferably used for this purpose. Special examples of such salt solutions are aqueous 0.5 mol/l potassium phosphate with a pH of 6.5 to 7.5 or a 2 to 5 mol/l NaCl with the same pH.

For chromatography on hydroxyapatite, salts, e.g. ammonium sulfate and especially phosphates, possibly present from preceding steps are removed from the protein solution, preferably by dialysis or ultrafiltration at membranes with an exclusion limit of 500 dalton prior to the application of the proteins to hydroxyapatite. Apart from viscosity increase by accompanying salts, however, only the phosphate concentration of the protein solution is critical for the chromatography on hydroxyapatite. The angiotropins are eluted by a potassium phosphate concentration gradient which is preferably linear. The angiotropins containing fractions are collected and then concentrated in the manner described below.

The use of hydroxyapatite is of essential significance for the structure-conserving isolation of pure angiotropins. However, in general, for technical and economic reasons, considerable difficulties arise from chromatography of larger volumes of protein solutions on hydroxyapatite columns. On the one hand, larger protein amounts contribute to the strong tendency of hydroxyapatite to clog, thus becoming unusable as stationary matrix in chromatography. On the other hand, hydroxyapatite is very expensive. Its use on larger scales is not ecnomical. For these reasons, in the process of the invention, the separation of a large part of the accompanying foreign proteins by appropriate biotechnical purification steps from the angiotropin-containing protein fractions is preferred for considerably reducing the volume of the protein solution prior to its chromatography on hydroxyapatite.

In the zone precipitation chromatography (cf. J. Porath, Nature, vol. 196 (1962); p. 47–48), residual protein contaminations in the angiotropins are separated by salting-out fractionation of the proteins by means and along a salt concentration gradient. The basic principle of separation of proteins in zone precipitation chromatography are different, structure-related, reversible solubility characteristics of proteins. They belong to the most sensitive molecular separation criteria and are often used for demonstration of molecular homogeneity of a protein. Two variants of this technique for development of the chromatogram are known: Fractional precipitation zone chromatography and fractional elution zone chromatography. Both types of techniques may have selective advantages in specific cases as described for fractional precipitation and fractional elution methods in protein separation. Temperature and pH, column characteristics can all be varied within relatively wide limits.

The temperature for zone precipitation chromatography can be between 0° and 40° C. Preferably, a temperature range from about 0° to 10° C. is used, especially from about 4° to 6° C. The pH can be between 4 and 10; preferably, a pH range of 6 to 8 is used, especially a pH of about 7. The length-to-diameter ratio of the column used should be greater than about 10:1. A ratio of 30 to 100:1 and especially of about 50:1 is preferred. All protein-compatible salts having salting-out properties for proteins are suitable. Examples of such salts are sodium-potassium phosphate, ammonium sulfate, and sodium sulfate. Ammonium sulfate is preferred.

The salt concentration gradient can have any desired shape provided that salting-out criteria of proteins achieve protein separation. Linear concentration gradients are preferred, especially an ascendent linear concentration gradient from 25 to 100% ammonium sulfate saturation. The maximum column charge is about 5% and preferably about 1% of total column volume.

The recycling or cascade molecular sieve filtration can be performed under the conditions described above for the analytical molecular sieve filtration. The same molecular sieves and the same column conditions can be used. Sephadex G 50 as stationary matrix is preferred in a column of a length-to-diameter ratio of at least about 50:1 and a maximum charge of about 3% of the column volume. The solvents used in the analytical molecular sieve filtration are also preferred as solvents for the elution in this method.

In recycling molecular sieve filtration, the distribution equilibria are disturbed continuously and the eluate is recycled onto the same column with fixed separation limits. In this way, the separation length of the migrating protein distribution bands are differentially extended. Alternatively, in cascade molecular sieve filtration, distribution equilibria are disturbed by continuous transfer of the eluate into a new second column with the same or similar, defined parameters at fixed separation limits.

Between the above-described purification steps, and if necessary at any stage for special purposes, protein solutions can be separated and freed from unwanted salts and water as well as concomitantly concentrated. The concentration (separation of a major portion of aqueous salt solution of the protein) can be achieved in different ways. Dehydration dialysis or ultrafiltration against protein-compatible liquid, preferably a sodium potassium phosphate buffer, are such methods. Dehydration dialysis is carried out preferably against polyethylene glycol (molecular weight 20,000 dalton) at membranes with exclusion limites of preferably 500 dalton. Ultrafiltration is preferably achieved at membranes with an exclusion limit of about 500 dalton. Small amounts of protein precipitates formed are removed by intermediary centrifugation to result in a clear protein solution. A desalting molecular sieve filtration on matrices with appropriate separation and exclusion limits can as well be used for this purpose, e.g. on Sephadex G 10, G 15 or G 20 as matrices. Furthermore, by selecting an appropriate mobile phase in the usual way, a usual molecular sieve filtration step can also be used concomitantly for this purpose.

To prevent sulfhydryl group oxidation, about 0.001 mol/l of cystein is preferably added to protein solutions throughout.

In the molecular sieve filtration purification steps about 0.4 mol/l ammonium sulfate is preferably added to the protein solution. In contrast to higher concentrations of this salt, at this concentration ammonium sulfate exerts a strong salting-in effect on proteins. Thus, proteins are better kept in solution during the molecular sieve filtration. Moreover, ammonium sulfate prevents growth of microorganisms and inhibits certain enzymes. Hence, it contributes to stabilization of the angiotropin structure which is important when chromatography is performed at higher temperature (above about 20° C.) and under nonsterile conditions.

Angiotropins which can be salted out are preferably completely precipitated alone or together with accompanying proteins by adding ammonium sulfate up to a concentration of about 3.25 to 3.7 mol/l (80 to 90% saturation). For this purpose 630 g/l ammonium sulfate are added (about 90% saturation). The pH value is preferably kept between 4 and 9 and the temperature up to 40° C., preferably between 0° and 8° C. The angiotropin-containing protein precipitate is separated from the protein-free supernatant solution by filtration, decantation or centrifugation. Unless otherwise stated centrifugation is preferably carried out at least at 10,000×g for a minimum of 45 min, and preferably for 1 h, in a one-step process. Or it can be carried out in two stages, at lower forces in the first stage for removal of the bulk of precipitated proteins; and then, for the supernatant of the first stage containing residual fine protein particles at higher forces, e.g. 20,000 to 50,000×g, by flow-through centrifugation.

The temperature and pH conditions during performance of the purification steps are not particularly critical. If the native conformation of the protein is to be preserved, an optimum temperature range is about 0° to 80° C., and preferably about 0° to 4° C. Moreover, the separation and purification steps must be carried out under essentially physiological pH and salt conditions. An essential advantage of the process of the invention consists in that these conditions are for the first time easy to adhere to.

The angiotropins obtained can be stored in a buffered physiological saline, e.g. in 0.0015 mol/l sodium-potassium phosphate solution containing 0.15 mol/l (0.9 w/v%) NaCl, 0.001 mol/l cysteine and having a pH of 7.4. After usual sterilization by filtration (pore diameter 0.2 μm), the protein preparation remains native and biologically active at room temperature for at least 200 h or frozen at −25° C. for at least 5 years. This stability of the protein can be considered, among others, to be one of the criteria of molecular homogeneity. Angiotropin solutions are safely stored at temperatures of between −20° and +50° C. in the presence of 2.0 to 3.6 mol/l ammonium sulfate (50 to 90% saturation). At this high osmotic pressure angiotropin solutions are protected against infection and degradation by microorganisms and bacterial growth. For their physiological, therapeutical and any other use, the angiotropins are again freed from salts by dialysis or ultrafiltration against an appropriate saline as described above.

The invention will now be given in detail by examples describing the isolation of the angiotropin protein preparation starting from leukocytes of porcine blood. However, the invention is not restricted to this embodiment. Leukocytes and inflamed tissues of other mammalians can be used too.

EXAMPLE A

PREPARATION OF ANGIOTROPINS FROM SUPERNATANTS OF CULTURES OF A MIXED POPULATION OF VIABLE LEUKOCYTES

The production of angiotropins in a culture solution of a mixed population of leukocytes and the separation of monocyto-angiotropic (MAT) and granulocyto-angiotropin (GAT) from the other components of the culture supernatant are described. All process steps are carried out at 0° to 8° C. in the presence of 0.001 mol/l cysteine, unless otherwise specified. The centrifugation is carried out in the manner described, either as a one or two step procedure (as flowthrough centrifugation).

A. 1. Preparation and culture of a mixed population of viable leukocytes 50 kg (about $10^{14}$) leukocytes are isolated as mixed cell population of physiological composition from 10,000 l of porcine blood and cultured in 20 batches of 2.5 kg (about $5 \times 10^{12}$ cells) under sterile conditions. The medium indicated in table III is used as culture solution. 50 l of culture medium are used per batch. Culturing is performed in glass vessels (Duran 50 or Pyrex glass). Initially, the cell density is about $10^8$ cells/ml. The culture is maintained at 37° C. in an atmosphere of 1 v/v % $CO_2$ over 40 hours. During this period, the cell suspension is slowly stirred (to r.p.m.) and flooded with sterile, waterwashed and heat-decontaminated air bubbles (<1 mm). The heat-decontamination of air is performed at about 500° C. by flowing through a silica tube. In addition to the partial oxygen pressure, the pH value (7.1) and the D-glucose level are measured and maintained constant. During culturing, the cells are induced to mitosis by the polyvalent mitogen content (CON) of the culture medium. The number, differential and morphological viability (dye exclusion test) of the cells are continuously determined by usual methods of hematology and cell culture techniques. The functional viability of cells is measured by their motility and their ability to respond to chemokinetic and chemotactic proteins. Mitoses are determined by chromosome count. The morphological viability of the cells after their biotechnical culturing is 95%. The entire loss in cells (mainly granulocytes) during culturing is at most 20% which is normal for primary cell cultures.

The culture is terminated by separating the cells from the supernatant solution by centrifugation for 10 minutes at 400×g and 10° C. The cells are washed twice in a salt solution containing 0.15 mol/l NaCl, 0.0015 mol/l sodium potassium phosphate and having the pH-value 7.1. They can be used for another purpose.

The culture supernatant solution is then centrifuged again for 1 hour at 10,000×g and at 4° C. to remove suspended particles. The resultant clear supernatant culture solution which has a total volume of 1000 liters and contains about 1,400 g protein as well as other macromolecules and salts is directly subjected to salting-out fractionation with ammonium sulfate (A2). Unless otherwise stated, all further steps are carried out at 0°–4° C.

A.2. First purification step (salting-out fractionation): Preparation of crude protein concentrate fractions 0.5 mol/l sodium-potassium phosphate buffer solution with a pH value of 6.7 is added to the supernatant culture solution (A 1) up to a final concentration of 0.1 mol/l. Furthermore, solid L-cystein is added up to a concentration of 0.001 mol/l.

This buffered supernatant culture solution is then adjusted to 35% saturation of ammonium sulfate by addition of 199 g of ammonium sulfate/l solution. During the addition, the pH-value of the protein solution is continuously controlled and maintained at 6.7 by the addition of 2 n ammonia. Part of the proteins is precipitated from the solution. The protein precipitate formed is separated from the supernatant containing salt-soluble proteins by centrifugation for 1 hour at 10,000×g. The precipitated crude protein fraction I is obtained as ammonium sulfate-containing protein sludge which contains about 100 g protein. This crude protein concentrate fraction I contains GAT and is separately processed for GAT according to the procedure described below.

Then the 35% salt-saturated supernatant culture solution is adjusted to 45% saturation of ammonium sulfate by adding 60 g of ammonium sulfate/l solution. The pH value of the protein solution is continuously controlled and maintained constant at 6.7 by 2 n ammonia. Another portion of proteins is precipitated from the solution. The protein precipitate is separated from the supernatant containing salt-soluble proteins by centrifugation for 1 hours at 10,000×g. The precipitated crude protein concentrate fraction II is obtained as ammonium sulfate-containing protein sludge, the protein content of which is about 60 g. This crude protein concentrate fraction II may be processed separately for its constituents, according to the procedure described below for the crude protein concentrate fraction III.

The 45% salt-saturated supernatant culture solution is then adjusted to 90% saturation of ammonium sulfate by adding 323 g of ammonium sulfate/l of solution. The pH-value of the protein solution is again continuously controlled and maintained constant at 6.7 by 2 n ammonia. Another portion of the proteins is precipitated from the solution. The protein precipitate is separated from the supernatant containing salt-soluble proteins by centrifugation for 1 hour at 10,000×g. The precipitated crude protein concentrate fraction III is obtained as ammonium sulfate-containing protein sludge the protein content of which is approximately 1,080 g. This fraction also contains the bulk of the serum albumin as component of the culture medium. This crude protein concentrate fraction III may be processed for its constituents according to the procedure described below. The 90% salt saturated supernatant fraction IV of the crude fraction III contains 160 g of salt-soluble proteins and other macro molecules (>500 daltons). This supernatant contains the MAT.

This salt-soluble protein-containing supernatant fraction IV is diluted with the same volume of the buffer solution A (0.15 mol/l NaCl, 0.0015 mol/l sodium-potassium phosphate, 0.001 mol/l L-cysteine, pH 7.4) to 45% saturation of ammonium sulfate and a maximum phosphate concentration of 0.05 mol/l. This solution is concentrated and desalted by ultrafiltration at a membrane with an exclusion limit of 500 dalton as a maximum. The salt-soluble proteins of this solution are obtained as crude retentate fraction IV in a volume of 13 l (about 100-fold concentration).

The crude protein concentrate fractions I, II and III and the retentate fraction IV are further purified. The fine purification of fraction I is described below under A 3 and applies to all crude protein concentrate fractions. The fine purification of the retentate fraction is mentioned below under A 4.

A.3. Fine purification of angiotropins in the crude protein concentrate fraction I A.3.1. Anion exchange chromatography The crude protein concentrate fraction I obtained above (A 2) is dissolved in a minimum volume of buffer solution B (0.01 mol/l of tris-HCl solution containing 0.04 mol/l NaCl and 0.001 mol/l cysteine and having a pH value of 8.0). The resultant slightly turbid solution (20 l) is clarified by centrifugation and then freed of salts by dialysis at a membrane with the exclusion limit of 500 dalton against buffer solution B until no sulfate ions are detectable. The clear solution obtained is then applied to a column of a swollen regenerated anion exchanger ($Cl^-$ as mobile exchangeable ion). It has a dextran matrix cross-linked with epichlorohydrin (DEAE-Sephadex A 50) which is equilibrated in the above-mentioned buffer system B.

The column has four times the volume of the protein solution and a length-to-diameter ratio of 10:1. The gel column is then washed with the above-mentioned adsorption buffer solution B until the extinction of the filtrate of 280 nm is ≦1.0.

For elution of the angiotropins and the adsorbed proteins, the charged ion exchanger gel is eluted with a NaCl-concentration gradient during 2 days. The gradient is linearly ascending from 0.4 to 2.0 mol/l NaCl, whereas the pH value, the tris/HCl and the cysteine concentrations are maintained constant. The same shape of gradient is then used for lowering the pH from 8 to 6.5 for further elution of the compounds. It is made up by 0.01 mol/l piperacine-HCl-buffer containing 2.0 mol/l NaCl and 0.001 mol/l cysteine and having the pH 6.5.

The angiotropin-containing fractions are collected and processed in further purification steps described below (A.3.2.–A.3.6).

A.3.2. Preparative molecular sieve filtration

After concentration of the proteins in the fractions (A.3.1) by salting-out precipitation with ammonium sulfate, the protein precipitate is dissolved in a minimum volume of buffer solution C (0.003 mol/l sodium-potassium phosphate containing 0.3 mol/l NaCl and 0.001 mol/l cysteine and having a pH value of 7.4). After removal of a small amount of insoluble compounds by centrifugation, the solution is applied to a column of a molecular sieve matrix of agarose crosslinked with acrylamide (Ultrogel AcA 34, particle size 60 to 160 μm) for preparative molecular sieve filtration. The column has 10 times the volume of the protein solution and a length-to-diameter ratio of 20:1. The column is then eluted with an upward flow (3 cm/h) of the mentioned buffer solution C. The fraction with the separation limits of 20,000 and 45,000 dalton is collected.

For the concentration of the proteins, the fraction is lyophilized, ultrafiltrated at a membrane with the exclusion limit of 500 dalton or adjusted to an ammonium sulfate concentration of 3.7 mol/l. In this case, the protein precipitates are separated from the supernatant by centrifugation and further processed as described below (A.3.3)

A.3.3 Cation exchange chromatography

The resultant GAT-containing protein precipitate (A 3.2) is dissolved in 1.5 volume parts of buffer solution D (0.01 mol/l sodium-potassium phosphate, 0.04 mol/l NaCl, 0.001 mol/l cysteine, pH 6.0). The solutions are centrifuged at 10,000×g for 1 hour for removal of a small amount of insoluble material.

The clear solution is dialyzed against the buffer solution D at a membrane with the exlusion limit of 500 dalton until no sulfate ions are detectable. The clear solution obtained is then applied to a column of swollen, regenerated cation exchanger, based on a dextran matrix cross-linked with epichlorohydrin (CM-Sephadex C 50). The exchanger is equilibrated in the above-mentioned buffer system D ($Na^+$ as mobile exchangeable ion).

The column has four times the volume of the protein solution and a length-to-diameter ratio of 10:1. The gel column is then washed with the above-mentioned adsorption buffer solution D, until the extinction of the filtrate at 280 nm is ≦1.0. The GAT is eluted in this step.

The GAT-containing fraction is collected and concentrated in the usual manner and further processed as described below (A.3.4).

A.3.4 Chromatography on hydroxyapatite

The GAT-containing protein precipitate (A.3.3) is dissolved in a minimum volume of 0.0001 mol/l sodium-potassium phosphate buffer solution E containing 0.001 mol/l cysteine and having a pH of 7.20. The solutions are then desalted with this buffer by molecular sieve filtration, ultrafiltration or dialysis (exclusion limit 500 dalton), until no sulfate is detectable in the dialysis buffer. Thereafter, a small portion of insoluble material is removed by centrifugation at 10,000×g for 1 hour.

The clear GAT-containing protein solution obtained is separately applied to a column of hydroxyapatite. The length-to-diameter ratio of the column is 10:1 and it has four times the volume of the protein volume to be applied. The column has been equilibrated with the mentioned buffer E used in an amount five times the column volume (flow 3 cm/h).

The negatively adsorbed proteins are washed out with the buffer solution E used for equilibrating the column. The elution of the GAT-containing fractions is carried out with a phosphate concentration gradient for 4 days. The gradient is linearly ascending from 0.0001 mol/l to 0.5 mol/l sodium-potassium phosphate having a constant pH value of 7.4 constant cysteine concentration. GAT is eluted at an average phosphate concentration of about 0.15 mol/l. The elution gradient is measured and controlled by means of conductivity. The GAT-containing fractions are concentrated in the usual manner and further processed as described below (A.3.5).

A.3.5. Zone precipitation chromatography

The GAT-containing fractions (A.3.4.) are dissolved in 0.1 mol/l sodium-potassium phosphate solution F containing 0.1 mol/l NaCl, 0.001 mol/l cysteine and 1 mol/l ammonium sulfate and having a pH value of 7.4. The resultant solution is applied at a temperature of 4° C. to a column of swollen molecular sieve matrix of dextran cross-linked with epichlorohydrin (Sephadex G-25). In the matrix, an ascendent, linear ammonium sulfate concentration gradient is established with the mobile buffer phase from 1.0 to 4.0 mol/l ammonium sulfate (20 to 100% saturation). The slope of the gradient is +2% of the ammonium sulfate saturation/cm of column height (0.08 mol/l $(NH_4)_2SO_4$/cm). The range of the gradient extends over approximately half the length of the column.

The length-to-diameter ratio of the column is 50:1, the column volume is 100 times higher than the protein solution volume to be applied. The flow rate is 2 cm/h.

The elution is carried out with the above-mentioned sodium-potassium phosphate solution F containing 1 mol/l of ammonium sulfate. The GAT-containing fractions which are eluted at 33% ammonium sulfate saturation are collected. The proteins are concentrated in the usual manner and further processed as described below. (A.3.6).

A.3.6. Analytical recycling molecular sieve filtration

The GAT-containing fractions (A.3.5.) are dissolved in buffer C (0.003 mol/l sodium-potassium phosphate containing 0.3 mol/l NaCl and 0.001 mol/l casteine and having a pH value of 7.4). Removal of a small portion of insoluble substances is achieved by centrifugation for 30 minutes at 48,000×g.

The resultant clear solution is then subjected to analytical recycling molecular sieve chromatography. For this purpose, the solution is applied at a temperature of 4° C. to a column of Ultrogel AcA 44 having a particle size of 60 to 140 μm. The column has 50 times the volume of the protein solution and a length-to-diameter ratio of 50:1. The elution is carried out with the mentioned buffer C. The eluates are recycled three times at a separation limit of 40,000 dalton. After usual protein concentration, approximately 8 mg of GAT are obtained having a molecular homogeneity of >95%, as indicated by conventional methods.

A.4. Fine purification of angiotropins in the retentate fraction IV

The retentate fraction IV (A.2) is purified in the manner described above for the crude protein concentrate fraction I. However, the sequence of the steps of preparative molecular sieve filtration and anion exchange chromatography is exchanged. Moreover, in the preparative molecular sive filtration and in the analytical recycling molecular sieve filtration, the Ultrogel AcA is replaced by a molecular sieve matrix of dextran which is cross-linked with epichlorohydrin (Sephadex G-50) and has a particle size of 40 to 120 and 20 to 80 μm, respectively.

In the preparative molecular sieve filtration, the separation limits are 7,000 to 3,000 dalton. In the chromatography on hydroxyapatite the MAT is eluted at an average phosphate concentration of 0.001 mol/l. In the zone precipitation chromatography, the MAT is eluted in the front distribution. In the analytical recycling molecular sieve filtration, the eluate is recycled at a separation limit of 7,000 dalton. The MAT yield is about 8 mg and has a molecular homogeneity of >95%, as shown by conventional methods.

In the following flow sheet, the above-described process for preparing the angiotropins of the invention is schematically represented.

| FLOW SHEET FOR BIOTECHNICAL PURIFICATION OF LEUKOCYTE - DERIVED ANGIOTROPINS | | | |
|---|---|---|---|
| Step | | STERILE CELL CULTURE | |
| 1st | | CELL CULTURE SUPERNATANT | |
| 2nd | | SALTING-OUT PRECIPITATION WITH AMMONIUM SULFATE | |
|  | ↓ 45% SATURATION FRACTION | | ↓ >90% SATURATION FRACTION (SOLUBLE) |
| 3rd | ↓ ANION EXCHANGE CHROMATOGRAPHY | | ↓ ULTRAFILTRATION, EXCLUSION >500 d |
| 4th | ↓ MOLECULAR SIEVE FILTRATION | | ↓ MOLECULAR SIEVE FILTRATION |
| 5th | ↓ CATION EXCHANGE CHROMATOGRAPHY | | ↓ ANION EXCHANGE CHROMATOGRAPHY |
| 6th | ↓ HYDROXYAPATITE CHROMATOGRAPHY | | ↓ CATION EXCHANGE CHROMATOGRAPHY |
| 7th | ↓ ZONE PRECIPITATION CHROMATOGRAPHY | | ↓ HYDROXYAPATITE CHROMATOGRAPHY |
| 8th | ↓ CASCADE MOLECULAR SIEVE FILTRATION | | ↓ ZONE PRECIPITATION CHROMATOGRAPHY |
| 9th | | | ↓ CASCADE MOLECULAR SIEVE FILTRATION |
|  | GRANULOCYTO - ANGIOTROPIN: | | MONOCYTO - ANGIOTROPIN: |

-continued

FLOW SHEET FOR BIOTECHNICAL PURIFICATION OF LEUKOCYTE - DERIVED ANGIOTROPINS

| 90'000 - FOLD PURIFIED, YIELD 8% | 120'000 - FOLD PURIFIED, YIELD 12% |

EXAMPLE B
PREPARATION OF ANGIOTROPINS FROM SUPERNATANTS OF CULTURES OF VIABLE MONOCYTES 3.5 kg (about $7 \times 10^{12}$) monocytes obtained from porcine blood are cultured under the conditions described in example A. During culture, the polyvalent mitrogen (CON) in the medium induces the mitosis of the cells.

The angiotropin MAT secreted to the culture solution is isolated according to the procedure described in Example A. It is thereby obtained in a highly purified state. The yield obtained is comparable to that of Example A.

EXAMPLE C
PREPARATION OF ANGIOTROPINS FROM INFLAMED TISSUE SITES

The preparation and isolation of angiotropins from inflamed tissue are described. 500 g of infarcted, inflamed canine heart muscle tissue are used. The heart muscle tissue is ground at 0°-4° C. 0.05 mol/l sodium potassium phosphate buffer solution containing 0.001 mol/l cystein and having a pH of 6.8 is added in a quantity three times the amount of the tissue. The resultant suspension is homogenized in a homogenizer (ultraturax). Thereafter, the supernatant containing the soluble compounds of the inflamed tissue is separated from the insoluble constituents by centriguation at $10,000 \times g$ and 4° C. The resultant supernatant solution is then centrifuged for 3 hours at $100,000 \times g$. The clear supernatant solution obtained is siphoned off from the flotating lipid layer. The angiotropin-containing clear supernatant protein solution is then subjected to fractional salting-out precipitation with ammonium sulfate according to Example A. The resultant protein fraction I and the concentrated retentate fraction IV are processed as described in Example A. From the 500 g tissue, angiotropins are obtained in a yield of approximately 0.03 mg of MAT, and about 0.02 mg of GAT.

EXAMPLE D
PREPARATION OF ANGIOTROPINS FROM LEUKOCYTE HOMOGENATES

Leukocytes are prepared from blood according to Example A. A homogenate of 500 g of leukocytes is prepared as shown in Example C. for muscle tissue. The isolation of the angiotropins contained in the leukocytes is performed according to Example A. The leukocytes cultured without stimulation contain only relatively small (about 1%) amounts of monocyte-angiotropins (MAT). The yields are approximately 5 µg of GAT and 1 µg of MAT.

What is claimed is:

1. Angiotropins of leukocytes and inflamed tissue, characterized by the following properties:
    (a) biological activities in vivo and in vitro:
        specific chemotropic action on blood vessels in vivo;
        induction of directional growth (chemotropism) of blood vessels along its concentration gradient;
        during vessel sprouting, tips of growing vessel capillaries have increased capillary permeability (FIG. 1);
        induction of neovascularization of tissues by directional in-growth of blood vessels (FIG. 1 and 2);
    (b) physico-chemical properties:
        electrophoretic migration in acrylamide matrices at a pH of 7.40 is anodic;
        soluble in aqueous media including in 20% ethanol at a pH value of at least 4.0 to 10;
        constant temperature coefficient of solubility in ammonium sulfate solutions between −10° C. and +50° C.;
        they absorb reversibly in structure and biological activity on anion and cation exchangers, calcium phosphate gel and hydroxyapatite and can be subjected in native form to volume partition chromatography.

2. Angiotropins according to claim 1, obtainable from leukocytes, by culturing leukocytes and isolation from the supernatant culture solution or from inflamed tissue.

3. Angiotropin (Monocyto-angiotropin) according to claims 1 or 2 characterized in that it is obtainable from mononuclear leukocytes and possesses the following additional properties:
    effective threshold dose in vivo: <2,5 fmol
    molecular weight of the native protein (primary structure); approximately 4,500 dalton;
    no protein quaternary structure in the form of physically bound peptide subunits: each of the native proteins consists of only one peptide unit
    soluble in an ammonium sulfate solution at 90% saturation (3.6 mol/l);
    it contains, amongst others, the amino acids tyrosine, phenylalanine, alanine, glycine, valine, cysteine and aspartic acid;
    absorption spectrum (UV, visible and near IR-range) as given in FIG. 3;
    extinction coefficients according to the following Table I:

TABLE I

| wave length, nm | $E_1$ mg/ml, 1 cm ($H_2O$, 20° C.) ± 6% |
|---|---|
| 250 (min) | 0.18 |
| 260 | 0.28 |
| 277 (max) | 0.49 |
| 280 | 0.48 |
| 290 | 0.30 |
| 400–1000 | 0 |
| $E_{280}/E_{260}$ | 1.71 |

4. Angiotropin (granulocyto-angiotropin) according to claims 1 or 2, characterized in that it is obtainable from granulocytes and possesses the following additional properties:
    effective threshold dose in vivo: <50 fmol
    molecular weight of the native protein (primary structure): approximately 35,000 dalton;
    insoluble in an ammonium sulfate solution at 35% saturation (1.4 mol/l);
    it contains, amongst others the amino acids tyrosine, phenylalanine, alanine, glycine, valine, cysteine, aspartic acid, proline and arginine;

absorption spectrum (UV, visible and near IR-range) according to FIG. 4;

extinction coefficient according to the following Table II:

TABLE II

| wave length, nm | $E_{1\ mg/ml,\ 1\ cm\ (H_2O,\ 20°\ C.)}$ + 6% |
|---|---|
| 250 (min) | 0.21 |
| 260 | 0.30 |
| 277 (max) | 0.59 |
| 280 | 0.58 |
| 290 | 0.35 |
| 400–1000 | 0 |
| $E_{280}/E_{260}$ | 1.93 |

5. A pharmaceutical composition for specifically influencing the angiogenesis and the vascular condition of a tissue of the body of mammalians, comprising an effective amount of at least one angiotropin according to any one of claims 1 to 4 together with a suitable carrier therefor.

6. A pharmaceutical composition for specifically influencing the angiogenesis and the vascular condition of a tissue of the body of mammalians, comprising an effective amount of at least one antiangiotropin-immunoglobulin and a suitable carrier therefor.

7. A method for specifically influencing the angiogenesis and the vascular condition of a tissue of the body of mammalians, which comprises administering an effective amount of at least one angiotropin according to anyone of claims 1 to 4.

8. A method for specifically influencing the angiogenesis and the vascular condition of a tissue of the body of mammalians, which comprises administering an effective amount of at least one anti-angiotropin immunoglobulin.

9. A process for producing and isolating angiotropins, which comprises:
   a. culturing a population of leukocytes in a suitable culture medium;
   b. separating the leukocytes from the culture medium after termination of culturing;
   c. adding a sufficient amount of a suitable salt to the culture solution to precipitate a first protein fraction from said culture medium;
   d. concentrating said salted culture medium to obtain a second protein fraction which is soluble therein; and
   e. separately purifying each of said first and second protein fractions by preparative and analytical molecular sieve filtration, anion and cation exchange chromatography, chromatography and hydroxyapatite, zone precipitation chromatography, and recycling or cascade molecular sieve filtration to obtain angiotropins.

10. The process according to claim 9, wherein a mixed leukocyte population is cultured.

11. The process according to claim 9, wherein a specific leukocyte type is cultured.

12. The process according to claim 9, wherein the leukocytes are cultured in a fully synthetic cell culture medium containing serum albumin as the only protein.

13. The process according to claim 9, wherein the mitosis of the leukocytes is induced during the culture.

14. The process according to claim 13, wherein a polyvalent mitogen and endotoxin-mitogen is added.

15. The process of claim 13, wherein an immune reaction is promoted on the cell surface so as to induce the mitosis of the leukocytes.

16. The process according to claim 14, wherein the mitosis of the leukocytes is induced by the addition of a lectin.

17. The process according to claim 16, wherein a lectin from Canavalia ensiformis (Concanavalin A=CON) is used.

18. The process according to claim 12, wherein the leukocytes are cultured in a cell culture medium having the composition given in Table III.

19. The process according to claim 18, wherein the leukocytes are cultured for approximately 40 hours, at a temperature of about 37° C., a concentration of about $10^7$ to $10^8$ cells/ml of culture medium and a $CO_2$-partial pressure of about 1% while sufficient oxygen is supplied to the culture.

20. The process according to claim 19, wherein ammonium sulfate is used to precipitate said proteins.

21. The process according to claim 20, wherein the ammonium sulfate concentration of the culture solution is increased stepwise and the proteins precipitated after each ammonium sulfate addition are separated from the culture solution thereby obtaining at least two crude protein fractions having differing solubilities at different ammonium sulfate concentrations.

22. The process according to claim 16, wherein the ammonium sulfate concentration of the culture solution is adjusted stepwise to 35%, 45% and 90% saturation.

23. The process according to claim 19, wherein the supernatant liquid is concentrated by ultrafiltration or dialysis after separation of the protein precipitate.

24. The process according to claim 9, wherein at least two of said purification steps are performed in sequence.

25. The process according to claim 24, wherein at least three of said purification steps are performed in sequence.

26. The process according to claim 9, wherein said anion and cation exchange chromatography steps are performed as batch adsorption processes.

27. A process for producing and isolating monocyto-angiotropin which comprises:
   a. culturing a leukocyte population in a culture medium;
   b. inducing the mitosis of the cells using CON during culturing;
   c. separating said cells from said medium;
   d. adding ammonium sulfate up to 90% saturation to said culture medium to precipitate proteins;
   e. separating the precipitated proteins from the ammonium sulfate containing supernatant;
   f. concentrating and purifying the supernatant by preparative molecular sieve filtration, anion exchange chromatography, cation exchange chromatography, hydroxyapatite chromatography, zone precipitation chromatography and recycling molecular sieve filtration; and
   g. isolating the monocyto-angiotropin in highly purified form from the eluate of recycling molecular sieve filtration, after separating the accompanying foreign proteins.

28. The process of claim 27, wherein said leukocyte population consists of monocytes.

29. The process of claim 27, wherein said leukocyte population is a mixed leukocyte population.

30. A process for producing and isolating granulocyto-angiotropin which comprises:
   a. culturing a leukocyte population;
   b. terminating the culturing;

c. adding sufficient ammonium sulfate to the culture solution to achieve up to a 35% saturation;

d. separating the precipitated proteins from the ammonium sulfate containing supernatant;

e. redissolving and purifying said proteins by anion exchange chromagraphy, preparative molecular sieve filtration, cation exchange chromatography, hydroxyapatite chromatography, zone precipitation chromatography and recycling molecular sieve filtration; and f. isolating the granulocyto-angiotropin in highly purified form from the eluate of recycling molecular sieve filtration, after separating the accompanying foreign proteins.

31. The process of claim 30, wherein said leukocyte population is a mixed leukocyte population.

32. The process of claim 30, wherein said leukocyte population consists of granulocytes.

33. The process of claim 30, further comprises inducing cell mitosis during culturing.

34. The process according to any one of claims 9 and 20 to 33, wherein the soluble portion of a leukocyte or inflamed tissue homogenate is used instead of the culture solution of the leukocytes.

35. Substantially pure monocytoangiotropin.

36. Substantially pure granulocytoangiotropin.

* * * * *